United States Patent [19]

Garrett et al.

[11] 4,393,066

[45] Jul. 12, 1983

[54] METHOD FOR TREATMENT OF HERPETIC LESIONS

[76] Inventors: David M. Garrett, 5711 39th St., Groves, Tex. 77619; Wallace R. Robin, 114 6th Ave., Nederland, Tex. 77627

[21] Appl. No.: 271,039

[22] Filed: Jun. 5, 1981

[51] Int. Cl.³ .......................................... A61K 31/505
[52] U.S. Cl. .................................................. 424/251
[58] Field of Search ........................................ 424/251

[56] References Cited

PUBLICATIONS

The Merck Index, 10th Ed., 1961, pp. 790–795, 1126–1128, 1441–1444.

Chemical Abstracts 82:144839w, (1975).
Sapiro, Sumner M., "Folic Acid Deficiency Preceding Non-Tropical Sprue", *Journal of Oral Medicine*, vol. 32, No. 4, 1977, pp. 106–109.
Vogel, Richard I., et al., "The Effect of Topical Application of Folic Acid on Gingival Health", *Journal of Oral Medicine* 33:2, Jan.–Mar., 1978.

*Primary Examiner*—Leonard Schenkman
*Attorney, Agent, or Firm*—Arnold, White & Durkee

[57] ABSTRACT

The instant invention relates to a method for treating vesicular lesions comprising the topical application at the lesion site to a patient suffering from said lesions of an amount of folic acid effective for treating said lesions.

1 Claim, No Drawings

METHOD FOR TREATMENT OF HERPETIC LESIONS

BACKGROUND OF THE INVENTION

This invention relates to a method for treating vesicular lesions. More particularly, this invention relates to a method of treating vesicular lesions comprising the topical administration to the lesion site of a person suffering from said lesions of an amount of folic acid effective for treating said lesions.

Vesicular lesions are generally characterized as acute errosive blister formations on the outer layer of skin and mucous membranes. Various vesicular lesions may be differentially diagnosed as herpes simplex type I (fever blisters), herpes simplex type II (a venereal form of herpes), herpes zoster (shingles), and aphthous ulcers (canker sores).

Herpes simplex, both type I and type II, is a recurrent acute viral infection exhibiting small grouped vesicles on an erythematous base. Such vesicles appear especially around the vermilion border of the lips and genitalia. Not uncommonly, outbreaks of herpes will involve regional lymphatic inflamation and tenderness. The principle symptoms complained of are burning and stinging localized at the site of the lesions. Clinical outbreaks, which may be recurrent in the same location for years, are exacerbated by fever, sunburn, wind burn, fatigue, stress, nervous tension, or mensturation.

Herpes zoster is an acute inflammatory viral disease exhibiting vesicular eruptions distributed unilaterally along the neural pathways of the trunk and face. Severe neurologic pain usually precedes the eruption of the vesicles by several days and may persist and actually increase in intensity after the lesions have disappeared.

Aphthous ulcers are shallow white mucosal ulcers having fairly even borders surrounded by erythema. Unlike the herpetic lesions which are a consequence of a viral infection, it has never been adequately demonstrated that the aphthous ulcers are due to a virus or any other specific chemical, physical or microbial agent.

Left to the natural course of healing, the various vesicular lesion diseases usually clear up from one to three weeks. During this period, a patient afflicted with such lesions, endures considerable pain, throbbing, burning sensation and pruritis localized about the lesion site. In many instances, irritation and persistance of the lesion may result in secondary bacterial infections which ultimately may lead to systemic complications and residual scarring.

Treatment for vesicular lesions has often been palliative rather than curative. For example, local anesthetics such as xylocaine or lidocaine may be applied to the lesion site to relieve the pain associated with the vesicular eruptions. However, such anesthetic treatment does not accelerate recovery of the lesion eruptions. One of the most widely recognized treatments for vesicular lesions is cauterization of the lesion site with silver nitrate. Silver nitrate, a very caustic agent, is applied locally to the lesion site to effect necrosis and eventual sloughing of the damaged lesion tissue. Unfortunately, such treatment in of itself is very painful and often results in residual scarring.

Other treatments for the virally induced lesions include antiviral agents such as Idoxuridine dissolved in dimethylsulfoxide or even diethyl ether engine starting fluid. The solvents, dimethylsulfoxide and diethyl ether, serve basically as anesthetic and drying agents to effect immediate relief of pain. Such treatments involving the use of these anesthetic solvents pose certain toxic side effects and have not yet been approved by the Food and Drug Administration.

In many instances, topical or systemic antibiotics are also prescribed as a measure to prevent secondary infections associated with the primary lesion outbreak. Antibiotics, however, are ineffective in limiting the course of the primary lesion duration. Other more exotic recommendations for treatment of herpetic vesicular lesions include periodic inoculation with small pox virus and chemotherapy with antineoplastic agents.

Despite the continued efforts of the medical profession to develop a treatment for accelerating the healing of vesicular lesions and alleviating the associated pain, the treatments offered heretofore have not provided an effective remedy which satisfies both objectives. Accordingly, there is a need for a simple, inexpensive, and effective treatment for vesicular lesions which both relieves localized pain and speeds tissue recovery.

SUMMARY OF THE INVENTION

This invention relates to a method for treating vesicular lesions which comprises the topical administration of a pharmaceutical preparation containing folid acid.

Traditionally, preparations of folic acid have been used systemically as hemotopoietic agents for the treatment of megaloblastic anemias, anemias associated with pregnancy, sprue, and related malabsorption syndromes. Further, folic acid has been administered as a vitamin supplement to patients exhibiting a depletion of folate reserves associated with oral contraceptive and anticonvulsant drug therapy and chronic alcoholism. To applicants' knowledge, others have not utilized folic acid in the manner specified in this application for the selective treatment of vesicular lesions.

DESCRIPTION OF PREFERRED EMBODIMENT

This invention relates to a method of treating vesicular lesions comprising topical administration to the lesion sites exposed by a patient suffering from said lesions, of an amount of a dilute folic acid preparation effective for treating said lesions.

Folic acid is generally recognized as a hemotopoietic vitamin present in liver, kidney, mushrooms, spinach, green leaves and grasses. Folic acid derived from these natural sources may exist in a free form having the general structure:

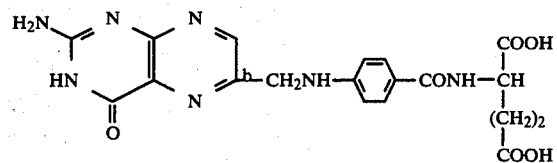

or may exist in combination with one or more additional molecules of (+)-glutamic acid. In addition to naturally derived sources, several synthetic mechanisms yielding folic acid have been described in the scientific literature and patents such as those issued to Merck & Co. (see for example U.S. Pat. Nos. 2,786,056; 2,816,109 and 2,821,527-8).

It is to be understood that, as used herein, "folic acid" is intended to be a collective generic term for each of the various conjugates of folic acid, including the substances hitherto known as folacin, folinic acid, citrovorum factor, leucovorin, pteroylglutamic acid either taken singularly or in combination, and pharmaceutically acceptable salts thereof.

Purified folic acid recrystallized from hot water is characterized as yellowish-orange crystals having an extremely thin platelet form. Spectral characteristics of folic acid derived from natural sources include a specific rotation of $[\alpha]_D^{25} 23°$ (concentration=0.5 gram folic acid in 100 ml 0.1 N NaOH); UV max (pH 13): 256, 283, and 368 nm.

More particularly, the treatment in accordance with this invention comprises the topical application to the site of vesicular lesions and surrounding tissue of a folic acid preparation. Various media may conveniently be employed as pharmaceutical vehicles incorporating folic acid, including but not limited to aqueous suspensions, alcoholic solutions and suspensions, lotions, creams and ointments.

Typically the concentration of folic acid incorporated into any one topical vehicle ranges from 0.5 to about 2.0 percent (weight/weight). Determination of a particular concentration of folic acid in a selected vehicle for topical application is ordinarily a function of pharmaceutical elegance, that is, providing folic acid in an aesthetically and tactile pleasing form. Because folic acid has relatively low solubility in various media, it is important to have a dilute concentration to prevent agglomeration, precipitation, granulation, or particulate crystallization of folic acid in the pharmaceutical preparation which may present skin irritation upon application. Moreover, since a topically applied medication is not normally subjected to the dilution factors inherent to systemic medication administration, there is no need to apply a highly concentrated formulation of folic acid to the lesion site.

An example of folic acid which may be utilized in the practice of the instant invention is Folvite ® available as 0.25 milligram and 1 milligram tablets and 0.5 percent parenteral injection available from Lederle Laboratories, a division of American Cyanamid Co., Pearl River, N.Y. Such compositions conform to U.S.P. standards. In the preparation of the folic acid composition of the instant invention, folic acid tablets are crushed or pulverized and then admixed into the selected pharmaceutical vehicle, typically a white petrolatum ointment base. Alternatively, the injectable form of folic acid may be incorporated directly within the selected vehicle base. However, the expense associated with the sterile injectable form may not economically justify its use when the less expensive powdered folic acid preparations are readily available.

In the preferred embodiment, the folic acid is incorporated into an adhesive base suitable for oral or mucosal application. Such an adhesive base is desirably Orabase ® marketed by Hoyt Laboratories, Needham, MA. Orabase ® is an oral protective paste comprising gelatin, pectin, sodium carboxymethyl cellulose in a plasticized hydrocarbon gel. This preparation provides a tenaciously adherent protective covering which protects the sensitive are against further irritation. The relative ratio of folic acid incorporated into Orabase ® is desirably 1.0 mg folic acid to 250 mg Orbase ®.

More particularly, treatment in accordance with this invention comprises topical application of a thin layer of the folic acid preparation to the lesion site and surrounding area. It is suggested that the patient apply the folic acid preparation with a cotton swab and rub the preparation into the lesion and surrounding area for a few seconds. Application is made from 4 to 6 times daily until healing is complete, usually within 3 to 5 days.

In extreme cases, involving lesion eruption and secondary bacterial infection, the folic acid may be incorporated into an antibiotic topical preparation. For example, folic acid may be admixed with a triple antibiotic ointment comprising neomycin sulfate, bacitracin, and polymyxin providing an effective combination treatment for both the primary vesicular lesions and the secondary bacterial infection.

The methods of the present invention have been utilized in treating the various herpes lesions and aphthous ulcers; however, this list is not intended to be exhaustive for all vesicular lesions for which this invention may be utilized. It should be appreciated that in view of the results obtained in the treatment of the herpes and aphthous ulcers, the methods of this invention are potentially useful for treatment of other vesicular lesions including those lesions associated with chicken pox, measles, impetigo, acne, poison ivy and poison oak.

To date approximately 50 patients have been treated according to the methods described by the present invention. All patients improved quickly, reporting immediate relief from pain and subsequent healing of lesions within 2 to 3 days.

In the normal course of treatment employing the methods of the present invention, immediate relief of pain on the order of minutes is noted upon application of the folic acid preparation. The analgesic effect provided by the folic acid preparation is not unlike the anesthetic effect provided by preparations such as lidocaine, xylocaine or benzocaine, however, pain relief is not as immediate with folic acid preparations as is effected by the classical anesthetics. Within hours, serous exudation from the lesions and subsequent drying is noted. Within 24 hours, the swelling around the lesion site diminishes and the redness subsides. Normally, within 48 hours there is a sloughing of scab tissue and healing is complete with only a slight redness evident or the prior lesion site. The use of the folic acid preparation also prevents subsequent festering and secondary bacterial infection often associated with untreated lesions.

The normal course of healing time for untreated lesions usually requires from 2 to 3 weeks, however according to the methods of the present invention healing of the primary lesion site is evident with 24 to 48 hours. Further, patients do not develop the more painful ulcerations or crusting lesions so typical of the normal course of natural lesion healing. Depending upon the degree of developmental stages of both the aphthous and herpes lesions, each stage improves dramatically within hours and pain is relieved soon after application.

The following discussion of case histories of patients treated according to the invention disclosed herein serves to illustrate the procedure employed in the teachings of the instant invention.

Case History A

A is 50 years old and the wife of a retired Army colonel. She has traveled extensively and tends to exhibit recurrent herpes eruptions under stress situation. She has sought medical attention in the past for the herpes eruptions but none of the past treatments have had any major impact. She has had small pox vaccinations to induce immunologic defenses but did not improve. At the first visit to the applicants' office she exhibited eruptions that were reaching the vesicular stage. She was placed on topical folic acid, specifically 1% folic acid in Neosporin ointment base (a product of Burroughs Wellcome comprising the three antibiotics (Polymixin B, Bacitracin, and Neomycin), according to the methods of the present invention. Upon application, the pain immediately subsided. Within 3 days there was only a slight pink area where the lesion had been. Patient stated that the scabbed area cleared within 48 hours.

Case History B

B is a 14 year old girl who has suffered recurrent herpetic lesions upon prolonged exposure to sunlight. At the time of B's visit to applicants' office she had a blistery eruption on the lower right lip. After applying the folic acid medication comprising 1% folic acid in Cortisporin ointment (a product of Burroughs Wellcome comprising Polymixin B, Bacitracin, Neomycin and Hydrocortisone) overnight, only a pinkish scar remained when she was examined the following day.

Case History C

C is a 60 year old male who complained of three herpetic type lesions on the lower lip. 1% folic acid in Orabase ® with white petrolateum was prescribed. After applying the medication, within 48 hours C reported that the vesicular lesions had cleared and he was experiencing no pain.

Case History D

D is a young professional, who occasionally suffers from aphthous ulcers. Upon experiencing the initial development of an aphthous ulcer, D applied a film of 1.0% folic acid in Orabase ®. After four applications of the medication over a two day period, D reported a clearing of the ulcer lesion.

In view of the foregoing description of the invention, further modifications and alternative embodiments of the method will be apparent to those skilled in the art. Accordingly, the foregoing description is to be construed as explanatory and illustrative only and is for the purpose of teaching and enabling those skilled in the art to treat vesicular lesions. While the preferred embodiment of the above-described invention is the best mode presently contemplated, it is by no means the only embodiment possible. The scope of the invention is defined by the following claims and also by all equivalent modification and variations that fall within the true spirit of the invention.

What is claimed is:

1. A method of treating herpetic lesions comprising the topical administration to the lesion site and surrounding tissue area of a patient suffering from said lesions of an amount of folic acid effective for treating said lesions.

* * * * *